US00PP26986P2

(12) United States Plant Patent
Kako et al.

(10) Patent No.: US PP26,986 P2
(45) Date of Patent: Jul. 26, 2016

(54) ***PETUNIA* PLANT NAMED 'SUNBUI MIHYAKU'**

(50) Latin Name: *Petunia×hybrida*
Varietal Denomination: Sunbui Mihyaku

(71) Applicants: Tetsuya Kako, Shimane (JP); Kiyoshi Miyazaki, Shiga (JP)

(72) Inventors: Tetsuya Kako, Shimane (JP); Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 171 days.

(21) Appl. No.: 13/999,250

(22) Filed: Jan. 31, 2014

(51) Int. Cl.
*A01H 5/02* (2006.01)

(52) U.S. Cl.
USPC ..... Plt./356.19

(58) Field of Classification Search
USPC ..... Plt./356.19
See application file for complete search history.

*Primary Examiner* — Keith Robinson
(74) *Attorney, Agent, or Firm* — C. A. Whealy

(57) ABSTRACT

A new and distinct cultivar of *Petunia* plant named 'Sunbui Mihyaku', characterized by its semi-trailing plant habit; vigorous growth habit; freely branching habit; early and freely flowering habit; long flowering period; large purple to purple violet-colored flowers; and good garden performance.

1 Drawing Sheet

Botanical designation: *Petunia×hybrida*.
Cultivar denomination: 'SUNBUI MIHYAKU'.

BACKGROUND OF THE INVENTION

The present invention relates to a new and distinct cultivar of *Petunia* plant, botanically known as *Petunia×hybrida* and hereinafter referred to by the name 'Sunbui Mihyaku'.

The new *Petunia* plant is a product of a planned breeding program conducted by the Inventors in Higashiomi, Shiga, Japan. The objective of the breeding program is to create new vigorous *Petunia* plants with a semi-trailing plant habit and numerous large attractive flowers.

The new *Petunia* plant originated from a cross-pollination made by the Inventors in March, 2011 in Higashiomi, Shiga, Japan of a proprietary selection of *Petunia×hybrida* identified as code name LNW, not patented, as the female, or seed, parent with a proprietary selection of *Petunia×hybrida* identified as code name Pri-198, not patented, as the male, or pollen, parent. The new *Petunia* plant was discovered and selected by the Inventors as a single flowering plant within the progeny of the stated cross-pollination in a controlled greenhouse environment in Higashiomi, Shiga, Japan in June, 2011.

Asexual reproduction of the new *Petunia* plant by terminal cuttings in a controlled greenhouse environment in Higashiomi, Shiga, Japan since June, 2011 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunbui Mihyaku'. These characteristics in combination distinguish 'Sunbui Mihyaku' as a new and distinct *Petunia* plant:

1. Semi-trailing plant habit.
2. Vigorous growth habit.
3. Freely branching habit.
4. Early and freely flowering habit.
5. Long flowering period.
6. Large purple to purple violet-colored flowers.
7. Good garden performance.

Plants of the new *Petunia* can be compared to plants of the female parent selection. Plants of the new *Petunia* differ primarily from plants of the female parent selection in plant habit as plants of the new *Petunia* are not as compact as plants of the female parent selection.

Plants of the new *Petunia* can be compared to plants of the male parent selection. Plants of the new *Petunia* differ primarily from plants of the male parent selection in flower size as plants of the new *Petunia* have larger flowers than plants of the male parent selection.

Plants of the new *Petunia* can also be compared to plants of the *Petunia×hybrida* 'USTUNI6001', disclosed in U.S. Plant Pat. No. 17,730. In side-by-side comparisons conducted in Higashiomi, Shiga, Japan, plants of the new *Petunia* and 'USTUNI6001' differed primarily in the following characteristics:

1. Plants of the new *Petunia* were taller than but not as broad as plants of 'USTUNI6001'.
2. Plants of the new *Petunia* had thicker stems than plants of 'USTUNI6001'.
3. Plants of the new *Petunia* had larger leaves than plants of 'USTUN6001'.
4. Plants of the new *Petunia* had larger flowers than plants of 'USTUNI6001'.
5. Petal margins of plants of the new *Petunia* were more undulate than petal margins of plants of 'USTUNI6001'.

6. Plants of the new *Petunia* and 'USTUNI6001' differed in flower color as plants of 'USTUNI6001' had bright pink-colored flowers.
7. Plants of the new *Petunia* had larger sepals than plants of 'USTUNI6001'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunbui Mihyaku' grown in a container.

The photograph at the bottom of the sheet is a close-up view of typical flowers and flower buds of 'Sunbui Mihyaku'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Petunia×hybrida* 'Sunbui Mihyaku'.

Parentage:

*Female, or seed, parent*.—Proprietary selection of *Petunia×hybrida* identified as code name LNW, not patented.

*Male, or pollen, parent*.—Proprietary selection of *Petunia×hybrida* identified as code name Pri-198, not patented.

Propagation:

*Type*.—By terminal cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; white in color.

*Rooting habit*.—Freely branching; dense.

Plant description:

*Plant form and growth habit*.—Semi-trailing plant habit; freely branching habit with numerous lateral branches developing per plant; pinching enhances lateral branch development; vigorous growth habit.

*Plant height*.—About 37.8 cm.

*Plant diameter*.—About 75.8 cm.

Lateral branch description:

*Length*.—About 44 cm.

*Diameter*.—About 2 mm.

*Internode length*.—About 2.6 cm.

*Strength*.—Strong, flexible.

*Aspect*.—Upright to outwardly.

*Texture*.—Densely pubescent; viscid.

*Color*.—Close to 144A.

Leaf description:

*Arrangement*.—Alternate, simple.

*Length*.—About 3.6 cm.

*Width*.—About 1.7 cm.

*Shape*.—Elliptical.

*Apex*.—Acute to broadly acute.

*Base*.—Obtuse.

*Margin*.—Entire.

*Texture, upper and lower surfaces*.—Pubescent.

*Venation pattern*.—Pinnate; reticulate.

*Color*.—Developing and fully expanded leaves, upper surface: Close to 138A; venation, close to 144B. Developing and fully expanded leaves, lower surface: Close to 138B; venation, close to 143C.

*Petioles*.—Length: About 5.5 mm. Diameter: About 2.6 mm. Texture, upper and lower surfaces: Pubescent. Color, upper and lower surfaces: Close to 144B.

Flower description:

*Flower arrangement and habit*.—Single salverform flowers arising from upper leaf axils; freely flowering habit with usually about 112 flowers developing per plant during the flowering season; flowers face upright to outwardly.

*Fragrance*.—None detected.

*Natural flowering season*.—Early flowering habit, plants of the new *Petunia* initiate and develop flowers about two to three weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower diameter*.—Relatively large, about 5.8 cm.

*Flower length (depth)*.—About 4.3 cm.

*Throat diameter*.—About 1.2 cm.

*Tube diameter, base*.—About 3.3 mm.

*Tube length*.—About 2.8 cm.

*Flower buds*.—Length: About 3.5 cm. Diameter: About 6.9 mm. Shape: Cylindrical; apex, twisting. Color: Close to N82B.

*Corolla*.—Arrangement: Five petals fused at the base and opening into a flared trumpet. Petal length from throat: About 2.5 cm. Petal width: About 2.3 cm. Petal shape: Spatulate. Petal apex: Mucronate. Petal margin: Entire; undulate. Petal texture, upper and lower surfaces: Smooth, glabrous; satiny Throat texture: Smooth, glabrous. Tube texture: Densely pubescent. Color: Petal, when opening, upper surface: Close to N78A; venation, close to N78A. Petal, when opening, lower surface: Close to N78B to N78C; venation, close to N79D. Petal, fully opened, upper surface: Close to N80A; venation, close to N78A; color does not change with development. Petal, fully opened, lower surface: Close to N78B; venation, close to N79D. Throat: Close to 150D; towards the petal lobes, close to 86C; venation, close to 79A. Tube: Close to N82C and 150D; venation, close to 142B.

*Calyx*.—Arrangement: One star-shaped calyx tube with five sepals in a single whorl and fused at the base. Sepal length: About 1.6 cm. Sepal width: About 4.6 mm. Sepal shape: Narrowly elliptic. Sepal apex: Obtuse. Sepal margin: Entire. Sepal texture, upper and lower surfaces: Pubescent. Color: Developing and fully developed sepals, upper surface: Close to 138A. Developing and fully developed sepals, lower surface: Close to 138B.

*Peduncles*.—Length: About 3.2 cm. Diameter: About 1.3 mm. Strength: Strong, flexible. Aspect: Upright to outwardly. Texture: Densely pubescent. Color: Close to 138A tinted with close to 59A.

*Reproductive organs*.—Stamens: Quantity per flower: Five. Stamen length: About 1.7 cm to 2.25 cm. Anther shape: Ellipsoidal. Anther size: About 2.2 mm by 2.7 mm. Anther color: Close to 91C. Pollen amount: Abundant. Pollen color: Close to N88B. Pistils: Quantity per flower: One. Pistil length: About 2.15 cm. Style color: Close to 144D. Stigma shape: Transversely ellipsoidal. Stigma color: Close to 146C. Ovary color: Close to 144B. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunbui Mihyaku' as illustrated and described.

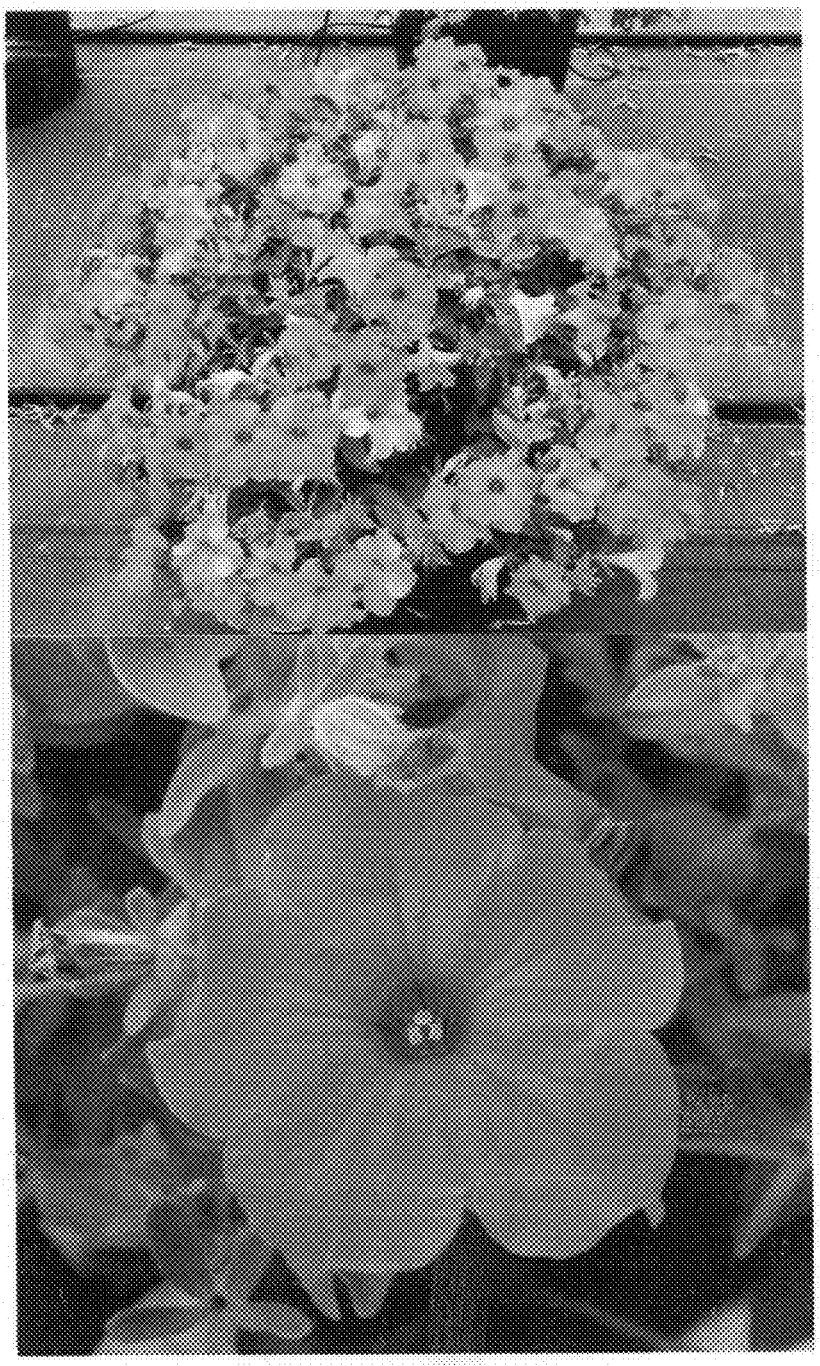

* * * * *